(12) United States Patent
Furman et al.

(10) Patent No.: US 6,410,546 B1
(45) Date of Patent: Jun. 25, 2002

(54) USE OF MKC-442 IN COMBINATION WITH OTHER ANTIVIRAL AGENTS

(75) Inventors: Phillip A. Furman; Cary P. Moxham, both of Durham; David W. Barry, Chapel Hill; Katyna Borroto-Esoda, Raleigh, all of NC (US)

(73) Assignee: Triangle Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 09/056,548

(22) Filed: Apr. 7, 1998

Related U.S. Application Data

(60) Provisional application No. 60/041,909, filed on Apr. 7, 1997.

(51) Int. Cl.[7] .................. A01N 43/54; A01N 43/90
(52) U.S. Cl. .................................... 514/274; 514/261
(58) Field of Search .............................. 514/274, 261

(56) References Cited

U.S. PATENT DOCUMENTS

| | | | | |
|---|---|---|---|---|
| 5,041,449 A | | 8/1991 | Belleau et al. ............. 514/274 |
| 5,047,407 A | | 9/1991 | Belleau et al. ............. 514/274 |
| 5,204,466 A | | 4/1993 | Liotta et al. ............... 544/317 |
| 5,210,085 A | * | 5/1993 | Liotta et al. ............... 514/274 |
| 5,234,913 A | | 8/1993 | Furman, Jr. et al. ......... 514/49 |
| 5,461,060 A | | 10/1995 | Miyasaka et al. .......... 514/269 |
| 5,466,806 A | | 11/1995 | Belleau et al. ............. 544/310 |
| 5,486,520 A | | 1/1996 | Belleau et al. ............. 514/274 |
| 5,532,246 A | | 7/1996 | Belleau et al. ............. 514/274 |
| 5,538,975 A | | 7/1996 | Dionne ...................... 514/256 |
| 5,604,209 A | * | 2/1997 | Ubasawa et al. ........... 514/45 |
| 5,618,820 A | | 4/1997 | Dionne ...................... 514/274 |
| 5,700,937 A | | 12/1997 | Liotta et al. ............... 544/317 |
| 5,728,575 A | | 3/1998 | Liotta et al. ............... 435/280 |
| 5,892,025 A | | 7/1998 | Liotta et al. ............... 536/46 |
| 5,814,639 A | | 9/1998 | Liotta et al. ............... 514/274 |
| 5,827,727 A | | 10/1998 | Liotta et al. ............... 435/280 |

FOREIGN PATENT DOCUMENTS

| | | |
|---|---|---|
| EP | 0382526 | 8/1990 |
| EP | 0515144 | 11/1992 |
| EP | 0515156 | 11/1992 |
| EP | 0515157 | 11/1992 |
| EP | 0526253 | 2/1993 |
| JP | 55-87777 | 7/1980 |
| WO | WO 91/11186 | 8/1991 |
| WO | WO 92/14743 | 9/1992 |
| WO | WO 94/14802 | 7/1994 |
| WO | WO 97/21706 | 6/1997 |

OTHER PUBLICATIONS

Abobo et al., Journal of Pharmaceutical Sciences, 83(1):96–99 (1994).
Baker et al., Journal of Medicinal Chemistry, 10(3):304–311 (1967).
Balzarini et al., Antimicrobial Agents and Chemotherapy, 39(4):998–1002 (1995).
Balzarini et al., Molecular Pharmacology, 49:882–890 (1996).
Benhida et al., Tetrahedron Letters, 37(7):1031–1034 (1996).
Brennan et al., Antiviral Research, 26:173–187 (1995).
Chemical Abstracts, 107:129717w (1987).
Chu et al., Journal of Medicinal Chemistry, 32: 612 (1989).
Drabikowska et al., 42(3):288–296 (1987).
Furman et al., Antimicrobial Agents and Chemotherapy, 36(12):2686–2692 (1992).
Hoong et al., Journal of Organic Chemistry, 57:5563–5565 (1992).
Jablonowski et al., AIDS Forshung (AIFO), 563–568 (1994).
Kilby, J. Michael and Michael S. Saag, Infectious Agents and Disease, 3(6):313–323.
Okamoto et al., Antiviral Research, 31:69–77 (1996).
Schinazi, r.F. et al., Antimicrobial Agents and Chemotherapy, 36(11):2432–2438.
Seki et al., Antiviral Chemistry & Chemotherapy, 6(2):73–79 (1995).
Smerdon et al., Proc. National Academy of Science USA, 91:3911–3915 (1994).
Wilson et al., Antimicrobial Agents and Chemotherapy, 37(8):1720–1722 (1993).
Yuasa et al., Molecular Pharmacology, 44:895–900 (1993).

* cited by examiner

*Primary Examiner*—Russel Travers
(74) *Attorney, Agent, or Firm*—Sherry M. Knowles, Esq.; Clark G. Sullivan, Esq.; King & Spalding

(57) ABSTRACT

Use of MKC-442 in combination with other antiviral agents for the treatment of patients infected with HIV is disclosed.

8 Claims, 2 Drawing Sheets

USE OF MKC-442 IN COMBINATION WITH OTHER ANTIVIRAL AGENTS

This application claims priority to U.S. Ser. No. 60/041,909, filed on Apr. 7, 1997, by Phillip A. Furman, Carey P. Moxham, David W. Barry and Katyna Dorroto-Esodo.

In 1983, the etiological cause of AIDS was determined to be the human immunodeficiency virus (HIV). In 1985, it was reported that the synthetic nucleoside 3'-azido-3'-deoxythymidine (AZT) inhibits the replication of human immunodeficiency virus. Since then, a number of other synthetic nucleosides, including 2',3'-dideoxyinosine (DDI), 2',3'-dideoxycytidine (DDC), and 2',3'-dideoxy-2',3'-didehydrothymidine (D4T), have been proven to be effective against HIV. After cellular phosphorylation to the 5'-triphosphate by cellular kinases, these synthetic nucleosides are incorporated into a growing strand of viral DNA, causing chain termination due to the absence of the 3'-hydroxyl group. They can also inhibit the viral enzyme reverse transcriptase.

The success of various synthetic nucleosides in inhibiting the replication of HIV in vivo or in vitro has led a number of researchers to design and test nucleosides that substitute a heteroatom for the carbon atom at the 3'-position of the nucleoside. European Patent Application Publication No. 0 337 713 and U.S. Pat. No. 5,041,449, assigned to BioChem Pharma, Inc., disclose racemic 2-substituted-4-substituted-1,3-dioxolanes that exhibit antiviral activity. U.S. Pat. No. 5,047,407 and European Patent Application No. 0 382 526, also assigned to BioChem Pharma, Inc., disclose that a number of racemic 2-substituted-5-substituted-1,3-oxathiolane nucleosides have antiviral activity, and specifically report that the racemic mixture of 2-hydroxymethyl-5-(cytosin-1-yl)-1,3-oxathiolane (referred to below as BCH-189) has approximately the same activity against HIV as AZT, with little toxicity. The (−)-enantiomer of the racemate BCH-189, known as 3TC, which is covered by U.S. Pat. No. 5,539,116 to Liotta et al., is currently sold for the treatment of HIV in combination with AZT in humans in the U.S.

It has also been disclosed that cis-2-hydroxymethyl-5-(5-fluorocytosin-1-yl)-1,3-oxathiolane ("FTC") has potent HIV activity. Schinazi, et al., "Selective Inhibition of Human Immunodeficiency Viruses by Racemates and Enantiomers of cis-5-Fluoro-1-[2-(Hydroxymethyl)-1,3-Oxathiolane-5-yl]Cytosine" *Antimicrobial Agents and Chemotherapy*, November 1992, pp. 2423–2431. See also U.S. Pat. No. 5,210,085; WO 91/11186, and WO 92/14743.

Another compound that exhibits efficacy against HIV both in vitro and in vivo is 6-benzyl-1-(ethoxymethyl)-5-isopropyluracil, which is also known as MKC-442.

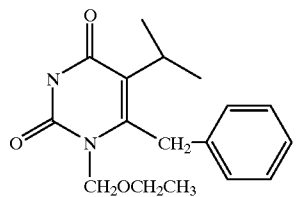

MKC-442 is described, for example, in U.S. Pat. No. 5,461,060.

MKC-442, although a nucleoside analogue, functions as a non-nucleoside reverse transcriptase inhibitor. It is considered an allosteric inhibitor because it appears to exert its activity by binding to an "allosteric position", i.e., one other than the binding site, of the enzyme. Preclinical tests suggest that MKC-442 may possess characteristics that address several of the therapeutic challenges of HIV. When tested in cell culture assay systems against wild-type (drug-sensitive) and several mutant strains of HIV known to be resistant to established non-nucleoside reverse transcriptase inhibitors, MKC-442 retained much of its ability to inhibit HIV replication. In these studies, MKC-442 displayed greater potency than nevirapine against wild-type and mutant strains of HIV. Preclinical studies of MKC-442 in two drug combinations with AZT or with DDI and in three drug combinations with AZT and saquinavir have demonstrated synergistic inhibition of HIV replication.

Studies in animals suggest a favorable safety and pharmacokinetic profile for MKC-442. Animal pharmacokinetic analyses showed good oral bioavailability and excellent penetration into the central nervous system, a significant site of HIV replication that is poorly penetrated by many currently marketed anti-HIV drugs. In rats, for example, the concentration of MKC-442 in the brain was 100% of that seen in the plasma.

A Phase I study evaluated the pharmacokinetics and tolerance of single escalating doses of MKC-442 in HIV-infected volunteers. The compound was generally well tolerated, with only a few participants experiencing minor adverse effects at the higher dose levels. In the groups receiving higher doses, concentrations of the drug in the plasma reached levels mich higher than the levels required to suppress 90% of the virus in culture.

Preliminary data from a Phase I/II double-blind, placebo controlled trial designed to evaluate the safety and efficacy of repeated multiple oral doses of MKC-442 in HIV-infected patients has now also been evaluated. A total of 49 patients were treated with MKC-442 for up to two months. Doses ranging from 100 mg to 1000 mg twice a day were given to groups of six to eight patients at each dosage level. At the highest doses tested (705 mg and 1000 mg twice a day), the viral load was reduced by an average of 96% in all patients after one week. This reduction was mostly sustained at two weeks whereafter it was followed by a gradual increase in viral load from the nadir toward baseline levels. A single point mutation at position 13 of the reverse transcriptase that may be associated with resistance was found in the virus obtained from some patients. In over 308 patient-weeks of drug exposure, MKC-442 was well tolerated.

It is known that over a period of time, agents such as MKC-442 that are active against HIV induce mutations in the virus which reduce the efficacy of the drug. There is a need to improve the durability of antiviral efficacy produced by antiretroviral drugs, including MKC-442, by decreasing the rate at which such mutations arise. Further, although MKC-442 exhibits a favorable pharmacokinetic and biodistribution profile, there is always a desire to improve these parameters. There is also a need to decrease the metabolism of the drug, which can lead to an increase in the plasma concentration of or exposure to MKC-442.

U.S. Pat. No. 5,604,209, issued on Feb. 18, 1997 to Ubasawa et al., and assigned to Mitsubishi Chemical Corporation, discloses that certain 6-benzyl-1-ethoxymethyl-5-substituted uracil derivatives, including MKC-442, and certain 2',3'-dideoxyribonucleosides, including 2',3'-dideoxyinosine (DDI), 3'-azido-3'-deoxythymidine (AZT), AZT triphosphate, and 2',3'-dideoxycytidine (DDC), exhibit a synergistic effect against HIV.

Japanese Patent Application No. 9-18384 filed on Jan. 31, 1997, by Mitsubishi Chemical Corporation, discloses a method for the treatment of HIV that includes the administration of a 6-benzyl-1-ethoxymethyl-5-substituted uracil derivative, including MKC-442, in combination with two or more nucleoside-type reverse transcriptase inhibitors or their esters, and in particular, those selected from the group consisting of AZT, 2',3'-dideoxy-3'-thiacytidine (3TC), PMEA (9-(2-phosphonylmethoxyethyl) adenine (Gilead); PMPA: (R)-9-(2-phosphonyl-methoxypropyl)adenine); 1592U89 succinate ((1S,4R)-4-[2-amino-6-cyclopropylamino)-9H-purin-9-yl]-2-cyclopentene-1-methanol succinate); 2',3'-dideoxyinosine (DDI); and 2',3'-dideoxy-2', 3'-didehydrothymidine (D4T), and esters thereof.

In light of the strong activity of MKC-442 against HIV, it is an object of the present invention to provide a method and composition that includes MKC-442 for the treatment of patients infected with HIV that exhibits advantageous or improved pharmacokinetic, biodistribution, metabolic, resistance or other parameters over administration of MKC-442 alone.

It is also an object of the invention to improve the efficacy of MKC-442 during short periods of administration and over extended time periods.

It is yet another object of the present invention to provide a method and composition for the treatment of patients infected with HIV in which MKC-442 is administered in combination or alternation with a second compound that acts synergistically with MKC-442 against the virus.

It is still another object of the present invention to provide a method and composition for the treatment of patients infected with HIV in which MKC-442 is administered in combination or alternation with a second compound (or at least one other compound) that acts synergistically with MKC-442 against the virus.

SUMMARY OF THE INVENTION

It has been discovered that MKC-442 can be administered in combination with one or more antiviral agents to achieve an advantageous therapeutic effect against HIV. In some cases, the enhanced therapeutic effect is not attainable by administration of either agent alone. In a preferred but not necessary embodiment, the effect of administration of the two agents in combination or alternation is synergistic.

In one preferred embodiment, MKC-442 is administered in combination with a protease inhibitor. In particular embodiments, MKC-442 is administered in combination or alternation with either indinavir, nelfinavir ([3S-[2(2S*, 3S*),3-alpha,4-a-beta,8a-beta-]]-N-(1,1-dimethylethyl) decahydro-2-)2-hydroxy-3-[(3-hydroxy-2-methylbenzoyl) amino]-4-(phenylthio)butyl]-3-isoquinolincarboxamide mono-methanesulfonate), saquinavir, or amprenavir (141 W94) (S)-tetrahydrofuran-3-yl-N-[(1S,2R)-3-[N-[(4-aminophenyl)-sulfonyl]-N-isobutylamino]-1-benzyl-2-hydroxypropyl]carbamate.

In another preferred embodiment, MKC-442 is administered in combination or alternation with a nucleoside analog such as abacavir (1592U89) which is (1S,4R)-4-[2-amino-6-cyclopropyl-amino)-9H-purin-9-yl]-2-cyclopentene-1-methanol succinate, 3TC, or FTC.

In another embodiment, MKC-442 is administered in combination with a non-nucleoside reverse transcriptase inhibitor, such as DMP-266 (efavirenz; (S)-6-chloro-4-(cyclopropylethynyl)-1, 4-dihydro-4-(trifluoromethyl)-2H-3, 1-benzoxazin-2-one), delavirdine (1-[3-(1-methylethyl)amino]-2-pyridinyl-4-[[5-[(methylsulfonyl)amino]-1H-indol-2-yl]carbonyl]-, monoethanesulfonate), or nevirapine.

In general, during alternation therapy, an effective dosage of each agent is administered serially, whereas in combination therapy, an effective dosage of two or more agents are administered together. The dosages will depend on such factors as absorption, biodistribution, metabolism and excretion rates for each drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions. Examples of suitable dosage ranges for protease inhibitors, including for example, nelfinavir and indinavir, can be found in the scientific literature and in the Physicians Desk Reference. Many examples of suitable dosage ranges for other compounds described herein are found in public literature or can be determined easily using known methods. These dosage ranges can be modified as desired to achieve a desired result.

The disclosed combination and alternation regiments are useful in the prevention and treatment of HIV infections and other related conditions such as AIDS-related complex (ARC), persistent generalized lymphadenopathy (PGL), AIDS-related neurological conditions, anti-HIV antibody positive and HIV-positive conditions, Kaposi's sarcoma, thrombocytopenia purpurea and opportunistic infections. In addition, these compounds or formulations can be used prophylactically to prevent or retard the progression of clinical illness in individuals who are anti-HIV antibody or HIV-antigen positive or who have been exposed to HIV.

DETAILED DESCRIPTION OF THE INVENTION

Figure 1:
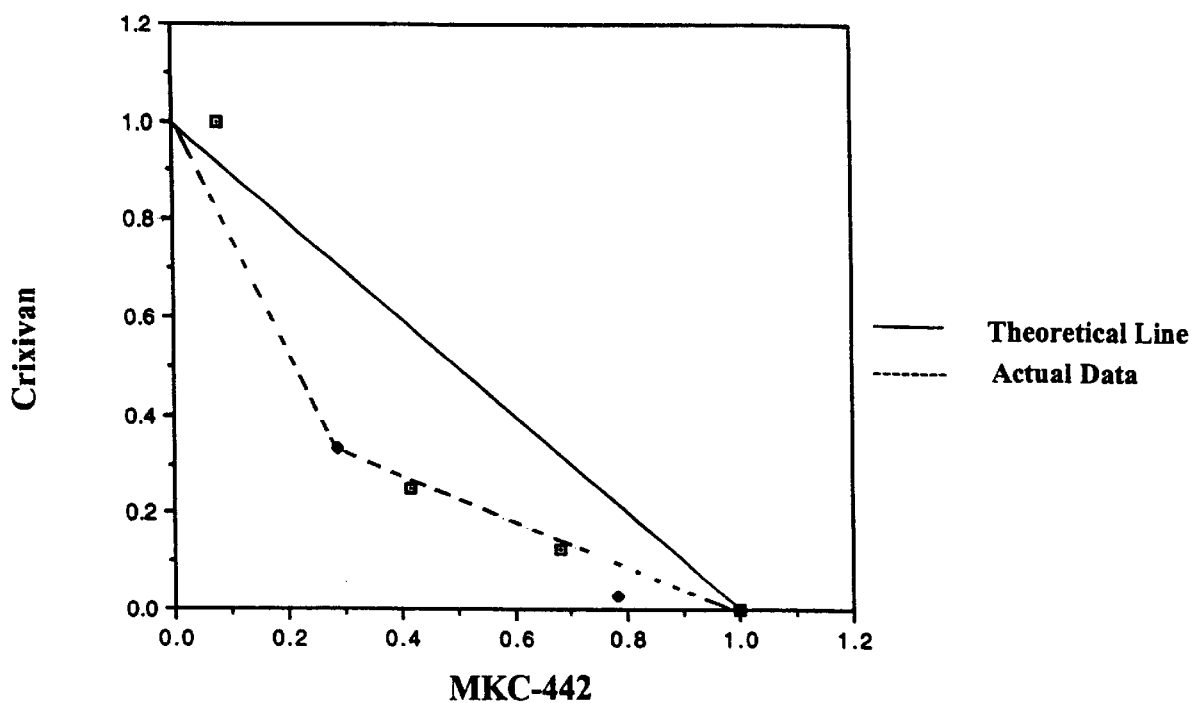
FIG. 1 is an isobologram analysis of the combination of MKC-442 and indinavir in cell culture.

It has been discovered that MKC-442 can be administered in combination with one or more antiviral agents to achieve an advantageous therapeutic effect to inhibit HIV replication. In most cases, the enhanced therapeutic effect is not attainable by administration of either agent alone. In a preferred but not necessary embodiment, the effect of administration of the two agents in combination or alternation is synergistic.

I. MKC-442 and Related Compounds

In one embodiment, an effective HIV-treatment amount of a compound of the formula:

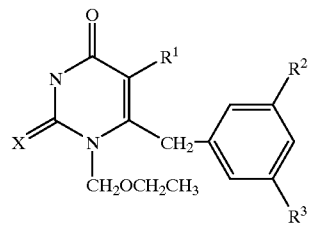

wherein X is oxygen or sulfur, $R^1$ is ethyl or isopropyl, $R^2$ and $R^3$ are independently hydrogen, $C_1$–$C_4$ alkyl or halogen (chlorine, bromine, iodine, or fluorine) is administered to a patient in need thereof in combination with a protease inhibitor or with another anti-HIV compound as described herein. In a preferred embodiment, the compound is MKC-442.

Any of the compounds described herein for combination or alternation therapy can be administered as any derivative that upon administration to the recipient, is capable of providing directly or indirectly, the parent compound, or that exhibits activity itself. Nonlimiting examples are the pharmaceutically acceptable salts (alternatively referred to as "physiologically acceptable salts"), and a compound which has been alkylated or acylated at an appropriate position. The modifications can affect the biological activity of the compound, in some cases increasing the activity over the parent compound. This can easily be assessed by preparing the derivative and testing its antiviral activity according to known methods.

As used herein, the term pharmaceutically acceptable salts refers to salts that retain the desired biological activity of the herein-identified compounds and exhibit minimal undesired toxicological effects. Non-limiting examples of such salts are (a) acid addition salts formed with inorganic acids (for example, hydrochloric acid, hydrobromic acid, sulfuric acid, phosphoric acid, nitric acid, and the like), and salts formed with organic acids such as amino acid, acetic acid, oxalic acid, tartaric acid, succinic acid, malic acid, ascorbic acid, benzoic acid, tannic acid, palmoic acid, alginic acid, polyglutamic acid, naphthalcnesulfonic acid, naphthalenedisulfonic acid, and polygalacturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like.

II. Combination or Alternation Therapy

It has been recognized that drug-resistant variants of HIV can emerge after prolonged treatment with an antiviral agent. Drug resistance most typically occurs by mutation of a gene that encodes for an enzyme used in the viral life cycle, and most typically in the case of HIV, in either the reverse transcriptase or protease genes. It has been demonstrated that the efficacy of a drug against HIV infection can be prolonged, augmented, or restored by administering the compound in combination or alternation with a second, and perhaps third, antiviral compound that induces a different mutation(s) from that selected for by the principle drug. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

The second antiviral agent for the treatment of HIV, in one embodiment, can be a protease inhibitor, or a reverse transcriptase inhibitor (a "RTI"), which can be either a synthetic nucleoside (a "NRTI") or a non-nucleoside compound (a "NNRTI"). In other embodiments, the second (or third) compound can be a pyrophosphate analog, or a fusion binding inhibitor. A list compiling resistance data collected in vitro and in vivo for a number of antiviral compounds is found in Schinazi et al., mutations in retroviral genes associated with drug resistance, *International Antiviral News*, Volume 1 (4), International Medical Press 1996.

In preferred embodiments, MKC-442 is administered in combination or alternation with FTC (2',3'-dideoxy-3'-thia-5-fluorocytidine); 141W94 (amprenavir, GlaxoWellcome, Inc.); Viramune (nevirapine), Rescriptor (delavirdine); or DMP-266 (efavirenz). In another preferred embodiment, MKC-442 is administered in combination or alternation with abacavir (1592U89), which is (1S,4R)-4-[2-amino-6-cyclopropyl-amino)-9H-purin-9-yl]-2-cyclopentene-1-methanol succinate.

Other examples of antiviral agents that can be used in combination or alternation with the compounds disclosed herein for HIV therapy include carbovir, acyclovir, interferon, stavudine, CS-92 (3'-azido-2',3'-dideoxy-5-methyl-cytidine), and β-D-dioxolane nucleosides such as β-D-dioxolanylguanine (DXG), β-D-dioxolanyl-2,6-diaminopurine (DAPD), and β-D-dioxolanyl-6-chloropurine (ACP).

Preferred protease inhibitors include indinavir ({1(1,S, 2R),5(S)]-2,3,5-trideoxy-N-(2,3-dihydro-2-hydroxy-1H-inden-1-yl)-5-[2-[[(1,1-dimethylethyl)amino]carbonyl]-4-(3-pyridinylmethyl)-1-piperazinyl]-2-(phenylmethyl)-D-erythro-pentoamide sulfate; Merck), nelfinavir (Agouron), ritonavir (Abbot), and saquinavir (Invirase; Roche).

Nonlimiting examples of other compounds that can be administered in combination or alternation with MKC-442 to augment the properties of the drug on administration include abacavir: (1S,4R)-4-[2-amino-6-cyclopropyl-amino)-9H-purin-9-yl]-2-cyclopentene-1-methanol succinate (1592U89, a carbovir analog; Glaxo Wellcome); AzddU:3'-azido-2',3'-dideoxyuridine; zidovudine: AZT, 3'-azido-3'-deoxythymidine (Glaxo Wellcome); BILA 1906: N-{1S-[[[3-[2S-{(1,1-dimethylethyl)amino]carbonyl}-4R-] 3-pyridinylmethyl)thio]-1-piperidinyl]-2R-hydroxy-1S-(phenylmethyl)propyl]amino]carbonyl]-2-methylpropyl}-2-quinolinecarboxamide (Bio Mega/Boehringer-Ingelheim); BILA 2185: N-(1,1-dimethylethyl)-1-[2S-[[2-2,6-dimethylphenoxy)-1-oxoethyl]amino]-2R-hydroxy-4-phenylbutyl]4R-pyridinylthio)-2-piperidinecarboxamide (Bio Mega/Boehringer-Ingelheim); BM+51.0836:triazoloisoindolinone derivative; BMS 186,318: aminodiol derivative HIV-1 protease inhibitor (Bristol-Myers-Squibb); d4API: 9-[2,5-dihydro-5-(phosphonomethoxy)-2-furanel]jadenine (Gilead); stavudine: d4T, 2',3'-didehydro-3'-deoxythymidine (Bristol-Myers-Squibb); efavirenz: DMP-266, a 1,4-dihydro-2H-3, 1-benzoxazin-2-one; HBY097: S-4-isopropoxycarbonyl-6-methoxy-3-(methylthio-methyl)-3,4-dihydroquinoxalin-2 (1H)-thione; HEPT:1-[(2-hydroxyethoxy)methyl]6-(phenylthio)thymine; KNI-272: (2S,3S)-3-amino-2-hydroxy-4-phenylbutyric acid-containing tripeptide; L-697, 593; 5-ethyl-6-methyl-3-(2-phthalimido-ethyl)pyridin-2 (1H)-one; L-735,524: hydroxy-aminopentane amide HIV-1 protease inhibitor (Merck); L-697,661: 3-{[(-4,7-dichloro-1,3-benzoxazol-2-yl)methyl]amino}-5-ethyl-6-methylpyridin-2(1H)-one; L-FDDC: (-)-β-L-5-fluoro-2',3'-dideoxycytidine; L-FDOC: (-)-β-L-5-fluoro-dioxolane cytosine; 6-benzyl-1-ethoxymethyl-5-isopropyluracil (I-EBU; Triangle/Mitsubishi); nevirapine: 11-cyclopropyl-5,11-dihydro-4-methyl-6H-dipyridol[3,2-b:2',3'-e]diazepin-6-one (Boehringer-Ingelheim); PFA: phosphonoformate (foscarnet; Astra); PMEA: 9-(2-phosphonylmethoxyethyl) adenine (Gilead); PMPA: (R)-9-(2-phosphonyl-methoxypropyl)adenine (Gilead); Ro 31-8959: hydroxyth-ethylamine derivative HIV-1 protease inhibitor (Roche); RPI-3121: peptidyl protease inhibitor, 1-[(3s)-3-(n-alpha-benzyloxycarbonyl)-1-asparginyl)-amino-2-hydroxy-4-phenylbutyryl]-n-tert-butyl-1-proline amide; 2720: 6-chloro-3,3-dimethyl-4-(isopropenyloxycarbonyl)-3,4-dihydro-quinoxalin-2(1H)thione; SC-52151: hydroxyethy-lurea isostere protease inhibitor (Searle); SC-55389A: hydroxyethyl-urea isostere protease inhibitor (Searle); TIBO R82150: (+)-(5S)-4,5,6,7-tetrahydro-5-methyl-6-(3-methyl-2-butenyl)imidazo[4,5,1-jk][1,4]-benzodiazepin-2(1H)-thione (Janssen); TIBO 82913: (+)-(5S)-4,5,6,7,-tetrahydro-9-chloro-5-methyl-6-(3-methyl-2-butenyl)imidazo[4,5,1jk]-[1,4]benzodiazepin-2(1H)-thione (Janssen); TSAO-m3T:[2', 5'-bis-O-(tert-butyldimethylsilyl)-3'-spiro-5'-(4'-amino-1', 2'-oxathiole-2',2'-dioxide)]-b-D-pentofuranosyl-N3-methylthymine; U90152: 1-[3-[(1-methylethyl)-amino]2-pyridinyl]-4-[[5-[(methylsulphonyl)-amino]-1H-indol-2yl]carbonyl]piperazine; UC: thiocarboxanilide derivatives (Uniroyal); UC-781=N-[4-chloro-3-(3-methyl-2-butenyloxy)phenyl]-2-methyl-3-furancarbothioamide; UC-82=N-[4-chloro-3-(3-methyl-2-butenyloxy)phenyl]-2-methyl-3-thiophenecarbothioamide; VB 11,328: hydroxyethylsulphonamide protease inhibitor (Vertex); VX-478: amprenavir, 141W94, hydroxyethylsulphonamide protease inhibitor (Vertex/Glaxo Wellcome); XM 323: cyclic urea protease inhibitor (Dupont Merck), delaviridine (Pharmacia Upjohn), famciclovir, gancyclovir, and penciclovir. In another embodiment, MKC-442 is administered in combination with LG1350, which has the following structure.

The nucleosides (or NNRTIs) can also be provided as a 5'-ether lipid, as disclosed in the following references, which are incorporated by reference herein: Kucera, L. S., N. Iyer, E. Leake, A. Raben, Modest E. K., D. L. W., and C. Piantadosi. 1990. "Novel membrane-interactive ether lipid analogs that inhibit infectious HIV-1 production and induce defective virus formation." *AIDS Res. Hum. Retro Viruses*. 6:491–501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest. 1991. "Synthesis and evaluation of novel ether lipid nucleoside conjugates for anti-HIV activity." *J. Med. Chem.* 34:1408.1414; Hosteller, K. Y., D. D. Richman, D. A. Carson, L. M. Stuhmiller, G. M. T. van Wijk, and H. van den Bosch. 1992. "Greatly enhanced inhibition of human immunodeficiency virus type 1 replication in CEM and HT4–6C cells by 3'-deoxythymidinc diphosphate dimyristoylglycerol, a lipid prodrug of 3,-deoxythymidine." *Antimicrob. Agents Chemother.* 36:2025.2029; Hostetler, K. Y., L. M. Stuhmiller, H. B. Lenting, H. van den Bosch, and D. D. Richman, 1990. "Synthesis and antiretroviral activity

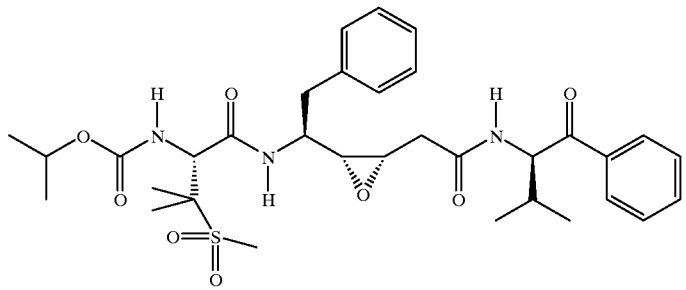

Nucleoside Prodrug Formulations

Any of the nucleosides or other compounds which are described herein for use in combination or alternation therapy with MKC-442 or its related compounds can be administered as an acylated prodrug or a nucleotide prodrug, as described in detail below.

The term acyl refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl.

Any of the nucleosides described herein (or NNRTIs) or other compounds that have a hdyroxyl group, or amine function, can be administered as a nucleotide or other prodrug to increase the activity, bioavailability, stability or otherwise alter the properties of the nucleoside. A number of nucleotide prodrug ligands are known. In general, alkylation, acylation or other lipophilic modification of the mono, di or triphosphate of the nucleoside will increase the stability of the nucleotide. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischofberger, *Antiviral Research*, 27 (1995) 1–17. Any of these can be used in combination with the disclosed nucleosides or other compounds to achieve a desire effect.

of phospholipid analogs of azidothymidine and other antiviral nucleosides." *J Biol. Chem.* 265:61127.

Nonlimiting examples of U.S. patents that disclose suitable lipophilic substituents that can be covalently incorporated into the nucleoside or other hydroxyl or amine containing compounds, preferably at the 5'-OH position of the nucleoside or lipophilic preparations, include U.S. Pat. No. 5,149,794 (Sep. 22, 1992, Yatvin et al.); U.S. Pat. No. 5,194,654 (Mar. 16, 1993, Hostetler et al., 5,223,263 (Jun. 29, 1993, Hostetler et al.); U.S. Pat. No. 5,256,641 (Oct. 26, 1993, Yatvin et al.); U.S. Pat. No. 5,411,947 (May 2, 1995, Hostetler et al.); U.S. Pat. No. 5,463,092 (Oct. 31, 1995, Hostetler et al.); U.S. Pat. No. 5,543,389 (Aug. 6, 1996, Yatvin et al.); U.S. Pat. No. 5,543,390 (Aug. 6, 1996, Yatvin et al.); U.S. Pat. No. 5,543,391 (Aug. 6, 1996, Yatvin et al.); and U.S. Pat. No. 5,554,728 (Sep. 10, 1996; Basava et al.), all of which are incorporated herein by reference. Foreign patent applications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

Nonlimiting examples of nucleotide prodrugs are described in the following references: Ho, D. H. W. (1973) "Distribution of Kinase and deaminase of 1β-D-arabinofuranosylcytosine in tissues of man and muse." *Cancer Res.* 33, 2816–2820; Holy, A. (1993) Isopolar phosphorous-modified nucleotide analogues," In: De Clercq (Ed.), *Advances in Antiviral Drug Design*, Vol. I, JAI Press, pp. 179–231; Hong, C. I., Nechaev, A., and West, C. R.

(1979a) "Synthesis and antitumor activity of 1β-D-arabinofuranosylcytosine conjugates of cortisol and cortisone." *Bicohem. Biophys. Rs. Commun.* 88, 1223–1229; Hong, C. I., Nechaev, A., Kirisits, A. J. Buchheit, D. J. and West, C. R. (1980) "Nucleoside conjugates as potential antitumor agents. 3. Synthesis and antitumor activity of 1-(β-D-arabinofuranosyl) cytosine conjugates of corticosteriods and selected lipophilic alcohols." *J. Med. Chem.* 28, 171–177; Hosteller, K. Y., Stuhmiller, L. M., Lenting, H. B. M. van den Bosch, H. and Richman *J. Biol. Chem.* 265, 6112–6117; Hosteller, K. Y., Carson, D. A. and Richman, D. D. (1991); "Phosphatidylazidothymidine: mechanism of antiretroviral action in CEM cells." *J Biol Chem.* 266, 11714–11717; Hosteller, K. Y., Korba, B. Sridhar, C., Gardener, M. (1994a) "Antiviral activity of phosphatidyl-dideoxycytidine in hepatitis B-infected cells and enhanced hepatic uptake in mice." *Antiviral Res.* 24, 59–67; Hosteller, K. Y., Richman, D. D., Sridhar. C. N. Felgner, P. L. Felgner, J., Ricci, J., Gardener, M. F. Selleseth, D. W. and Ellis, M. N. (1994b) "Phosphatidylazidothymidine and phosphatidyl-ddC: Assessment of uptake in mouse lymphoid tissues and antiviral activities in human immunodeficiency virus-infected cells and in rauscher leukemia virus-infected mice." *Antimicrobial Agents Chemother.* 38, 2792–2797; Hunston, R. N., Jones, A. A. McGuigan, C., Walker, R. T., Balzarini, J., and DeClercq, E. (1984) "Synthesis and biological properties of some cyclic phosphotriesters derived from 2'-deoxy-5-flourouridine." *J. Med. Chem.* 27, 440–444; Ji, Y. H., Moog, C., Schmitt, G., Bischoff, P. and Luu, B. (1990); "Monophosphoric acid esters of 7-β-hydroxycholesterol and of pyrimidine nucleoside as potential antitumor agents: synthesis and preliminary evaluation of antitumor activity." *J. Med. Chem.* 33 2264–2270; Jones, A. S., McGuigan, C., Walker, R. T., Balzarini, J. and DeClercq, E. (1984) "Synthesis, properties, and biological activity of some nucleoside cyclic phosphoramidates." *J. Chem. Soc. Perkin Trans.* I, 1471–1474; Juodka, B. A. and Smart, J. (1974) "Synthesis of diribonucleoside phosph (P→N) amino acid derivatives." *Coll. Czech. Chem. Comm.* 39, 363–968; Kataoka, S., Imai, J., Yamaji, N., Kato, M., Saito, M., Kawada, T. and Imai, S. (1989) "Alkylated cAMP derivatives; selective synthesis and biological activities." *Nucleic Acids Res. Sym. Ser.* 21, 1–2; Kataoka, S., Uchida, "(cAMP) benzyl and methyl triesters." *Heterocycles* 32, 1351–1356; Kinchington, D., Harvey, J. J., O'Connor, T. J., Jones, B. C. N. M., Devine, K. G., Taylor-Robinson D., Jeffries, D.J. and McGuigan, C. (1992) "Comparison of antiviral effects of zidovudine phosphoramidate and diphosphorodiamidate derivatives against HIV and ULV in vitro." *Antiviral Chem. Chemother.* 3, 107–112; Kodama, K., Morozumi, M., Saithoh, K. I., Kuninaka, H., Yosino, H. and Saneyoshi, M. (1989) "Antitumor activity and pharmacology of 1-β-D-arabinofuranosylcytosine -5'-stearylphosphate; an orally active derivative of 1-β-D-arabinofuranosylcytosine." *Jpn. J. Cancer Res.* 80, 679–685; Korty, M. and Engels, J. (1979) "The effects of adenosine- and guanosine 3',5' phosphoric and acid benzyl esters on guinea-pig ventricular myocardium." *Naunyn-Schmiedeberg's Arch. Pharmacol.* 310, 103–111; Kumar, A., Goe, P. L., Jones, A. S. Walker, R. T. Balzarini, J. and DeClercq, E. (1990) "Synthesis and biological evaluation of some cyclic phosphoramidate nucleoside derivatives." *J. Med. Chem*, 33, 2368–2375; LeBec, C., and Huynh-Dinh, T. (1991) "Synthesis of lipophilic phosphate triester derivatives of 5-fluorouridine an arabinocytidine as anticancer prodrugs." *Tetrahedron Lett.* 32, 6553–6556; Lichtenstein, J., Barner, H. D. and Cohen, S. S. (1960) "The metabolism of exogenously supplied nucleotides by *Escherichia coli.*," *J. Biol. Chem.* 235, 457–465; Lucthy, J., Von Daeniken, A., Friederich, J. Manthey, B., Zweifel, J., Schlatter, C. and Benn, M. H. (1981) "Synthesis and toxicological properties of three naturally occurring cyanoepithioalkanes". *Mitt. Geg. Lebensmittelunters. Hyg.* 72, 131–133 (*Chem. Abstr.* 95, 127093); McGigan, C. Tollerfield, S. M. and Riley, P. a. (1989) "Synthesis and biological evaluation of some phosphate triester derivatives of the anti-viral drug Ara." *Nucleic Acids Res.* 17, 6065–6075; McGuigan, C., Devine, K. G., O'Connor, T. J., Galpin, S. A., Jeffries, D. J. and Kinchington, D. (1990a) "Synthesis and evaluation of some novel phosphoramidate derivatives of 3'-azido-3'-deoxythymidine (AZT) as anti-HIV compounds." *Antiviral Chem. Chemother.* 1 107–113; McGuigan, C., O'Connor, T. J., Nicholls, S. R. Nickson, C. and Kinchington, D. (1990b) "Synthesis and anti-HIV activity of some novel substituted dialkyl phosphate derivatives of AZT and ddcyd." *Antiviral Chem. Chemother.* 1, 355–360; McGuigan, C., Nicholls, S. R., O'Connor, T. J., and Kinchington, D. (1990c) "Synthesis of some novel dialkyl phosphate derivative of 3'-modified nucleosides as potential anti-AIDS drugs." *Antiviral Chem. Chemother.* 1, 25–33; McGuigan, C., Devin, K. G., O'Connor, T. J., and Kinchington, D. (1991) "Synthesis and anti-HIV activity of some haloalkyl phosphoramidate derivatives of 3'-azido-3' deoxythymidine (AZT); potent activity of the trichloroethyl methoxyalaninyl compound." *Antiviral Res.* 15, 255–263; McGuigan, C., Pathirana, R. N., Balzarini, J. and DeClercq, E. (1993b) "Intracellular delivery of bioactive AZT nucleotides by aryl phosphate derivatives of AZT." *J. Med. Chem.* 36, 1048–1052.

Alkyl hydrogen phosphate derivatives of the anti-HIV agent AZT may be less toxic than the parent nucleoside analogue. *Antiviral Chem. Chemother5.*, 271–277; Meyer, R. B., Jr., Shuman, D. A. and Robins, R. K. (1973) "Synthesis of purine nucleoside 3', 5'-cyclic phosphoramidates." *Tetrahedron Lett.* 269–272; Nagyvary, J. Gohil, R. N., Kirchner, C. R. and Stevens, J. D. (1973) "Studies on neutral esters of cyclic AMP," *Biochem. Biophys. Res. Commun.* 55, 1072–1077; Namane, A. Gouyette, C., Fillion, M. P., Fillion, G. and Huynh-Dinh, T. (1992) "Improved brain delivery of AZT using a glycosyl phosphotriester prodrug." *J. Med. Chem.* 35, 3039–3044; Nargeot, J. Nerbonne, J. M. Engels, J. and Leser, H. A. (1983) *Natl. Acad. Sci. U.S.A.* 80, 2395–2399; Nelson, K. A., Bentrude, W. G. Stser, W. N. and Hutchinson, J. P. (1987) "The question of chair-twist equilibria for the phosphate rings of nucleoside cyclic 3', 5' monophosphates. $^1$HNMR and x-ray crystallographic study of the diastereomers of thymidine phenyl cyclic 3', 5'-monophosphatc." *J Am. Chem. Soc.* 109, 4058–4064; Nerbonne, J. M., Richard, S., Nargeot, J. and Lester, H. A. (1984) "New photoactivatable cyclic nucleotides produce intracellular jumps in cyclic AMP and cyclic GMP concentrations." *Nature* 301, 74–76; Neumann, J. M., Hervé, M., Debouzy, J. C., Guerra, F. I., Gouyette, C., Dupraz, B. and Huyny-Dinh, T. (1989) "Synthesis and transmembrane transport studies by NMR of a glucosyl phospholipid of thymidine." *J Am. Chem. Soc.* 111, 4270–4277; Ohno, R., Tatsumi, N., Hirano, M., Imai, K. Mizoguchi, H., Nakamura, T., Kosaka, M., Takatuski, K., Yamaya, T., Toyama K., Yoshida, T., Masaoka, T., Hashimoto, S., Ohshima, T., Kimura, I., Yamada, K. and Kimura, J. (1991) "Treatment of myelodysplastic syndromes with orally administered 1-β-D-arabinouranosylcytosine -5' stearylphosphate." *Oncology* 48, 451–455. Palomino, E., Kessle, D. and Horwitz, J. P. (1989) "A dihydropyridine carrier system for sustained delivery of 2', 3' dideoxynucleosides to the brain." *J. Med.*

Chem. 32, 22–625; Perkins, R. M., Barney, S. Wittrock, R., Clark, P. H., Levin, R. Lambert, D. M., Petteway, S. R., Serafinowska, H. T., Bailey, S. M., Jackson, S., Harnden, M. R. Ashton, R., Sutton, D., Harvey, J. J. and Brown, A. G. (1993) "Activity of BRL47923 and its oral prodrug, SB203657A against a rauscher murine leukemia virus infection in mice." *Antiviral Res.* 20 (Suppl. I). 84; Piantadosi, C., Marasco, C. J., Jr., Norris-Natschke, S. L., Meyer, K. L., Gumus, F., Surles, J. R., Ishaq, K. S., Kucera, L. S. Iyer, N., Wallen, C. A., Piantadosi, S. and Modest, E. J. (1991) "Synthesis and evaluation of novel ether lipid nucleoside conjugates for anti-HIV-1 activity." *J. Med. Chem.* 34, 1408–1414; Pompon, A., Lefebvre, I., Imbach, J. L., Kahn, S. and Farquhar, D. (1994). "Decomposition pathways of the mono-and bis(pivaloyloxymethyl) esters of azidothymidinc-5'-monophosphate in cell extract and in tissue culture medium; an application of the on-line ISRP-cleaning HPLC technique." *Antiviral Chem Chemother.* 5, 91–98; Postemark, T. (1974) "Cyclic AMP and cyclic GMP." *Annu. Rev. Pharmacol.* 14, 23–33; Prisbe, E. J., Martin, J. C. M., McGhee, D. P. C., Barker, M. F., Smee, D. F. Duke, A. E., Matthews, T. R. and Verheyden, J. P. J. (1986) "Synthesis and antiherpes virus activity of phosphate an phosphonate derivatives of 9-[(1,3-dihydroxy-2-propoxy)methyl] guanine." *J Med. Chem.* 29, 671–675; Pucch, F., Gosselin, G., Lefebvre, I., Pompon, a., Aubertin, A. M. Dirn, and Imbach, J. L. (1993) "Intracellular delivery of nucleoside monophosphate through a reductase-mediated activation process." *Antiviral Res.* 22, 155–174; Pugaeva, V. P., Klochkeva, S. I., Mashbits, F. D. and Eizengart, R. S. (1969). "Toxicological assessment and health standard ratings for ethylene sulfide in the industrial atmosphere." *Gig. Trf. Prof. Zabol.* 14, 47–48 (Chem. Abstr. 72, 212); Robins, R. K. (1984) "The potential of nucleotide analogs as inhibitors of Retro viruses and tumors." *Pharm. Res.* 11–18; Rosowsky, A., Kim. S. H., Ross and J. Wick, M. M. (1982) "Lipophilic 5'-(alkylphosphate) esters of 1-β-D-arabinofuranosylcytosine and its $N^4$-acyl and 2.2'-anhydro-3'0-acyl derivatives as potential prodrugs." *J Med. Chem.* 25, 171–178; Ross, W. (1961) "Increased sensitivity of the walker turnout towards aromatic nitrogen mustards carrying basic side chains following glucose pretreatment." *Biochem. Pharm.* 8, 235–240; Ryu, E. K., Ross, R. J. Matsushita, T., MacCoss, M., Hong, C. I. and West, C. R. (1982). "Phospholipid-nucleoside conjugates. 3. Synthesis and preliminary biological evaluation of 1-β-D-arabinofuranosylcytosine 5' diphosphate [-], 2-diacylglycerols." *J. Med. Chem.* 25, 1322–1329; Saffhill, R. and Hume, W. J. (1986) "The degradation of 5-iododeoxyuridine and 5-bromoethoxyuridine by serum from different sources and its consequences for the use of these compounds for incorporation into DNA." *Chem. Biol. Interact.* 57, 347–355; Saneyoshi, M., Morozumi, M., Kodama, K., Machida, J., Kuninaka, A. and Yoshino, H. (1980) "Synthetic nucleosides and nucleotides. XVI. Synthesis and biological evaluations of a series of 1-β-D-arabinofuranosylcytosine 5'-alky or arylphosphates." *Chem Pharm. Bull.* 28, 2915–2923; Sastry, J. K., Nehete, P. N., Khan, S., Nowak, B. J., Plunkett, W., Arlinghaus, R. B. and Farquhar, D. (1992) "Membrane-permeable dideoxyuridine 5'-monophosphate analogue inhibits human immunodeficiency virus infection." *Mol. Pharmacol.* 41, 441–445; Shaw, J. P., Jones, R. J. Arimilli, M. N., Louie, M. S., Lee, W. A. and Cundy, K. C. (1994) "Oral bioavailability of PMEA from PMEA prodrugs in male Sprague-Dawley rats." *9th Annual AAPS Meeting.* San Diego, Calif. (Abstract). Shuto, S., Ueda, S., Imamura, S., Fukukawa, K. Matsuda, A. and Ueda, T. (1987) "A facile one-step synthesis of 5' phosphatidylnucleosides by an enzymatic two-phase reaction." *Tetrahedron Lett.* 28, 199–202; Shuto, S. Itoh, H., Ueda, S., Imamura, S., Kukukawa, K., Tsujino, M., Matsuda, A. and Ueda, T. (1988) *Pharm. Bull.* 36, 209–217.

An example of a useful phosphate prodrug group is the S-acyl-2-thioethyl group, also referred to as "SATE".

These compounds can be tested for synergistic activity with MKC-442 against HIV according to a number of assays, including that described below.

EXAMPLE 1

Evaluation of Inhibition of HIV Infection Using Combined Antiviral Agents

The inhibitory effects of combined antiviral agents were evaluated using the human T cell line, MT2. Infection of this cell line with HIV results in cell death. Inhibition of the HIV induced cytopathic effect by the combined agents is measured in a MTT (3-[4,5-dimethylthiazol-2-yl]-2,5-diphenyl tetrazolium bromide) based assay. The mitochondrial dehydrogenases of viable cells will cleave the tetrazolium ring of MTT, yielding purple formazan crystals which are soluble in acidified isopropanol. The resulting purple solution is measured spectrophotometrically. The amount of purple dye formed is directly related to the number of viable cells. Therefore, a decrease in color in this assay indicates cell death due to viral cytopathic effects (CPE). This assay has been employed in the assessment of a variety of antiretroviral compounds (Pauwels, R. et al, 1988, J. Virol. Methods, 20: 309–321.) and is readily adaptable to any system with a lytic virus.

Preparation of Drug Plates.

The assays are performed in a 96 well microtiter plate. Each compound to be tested is made up at 4 times the final concentration to allow for dilution by cells and other test compounds. Compounds are prepared in complete RPMI media (RPMI 1640 plus 10% fetal bovine serum plus 20 mg/mL gentamicin). Two drugs are tested simultaneously on each plate using a checkerboard design. Serial dilutions of the first drug are added to the vertical wells (50 mL/well) of the plate (columns 2–11). Serial dilutions of the second drug (50 mL/well) are then added to the plate across horizontal rows (rows A–G). Column #2 and row H contain dilutions of only one compound. $EC_{50}$ values obtained from these wells are a measure of the antiviral activity of each compound alone. Column #1 contains virus control, infected cells grown in the absence of compound, and Column 12 contains cell control, mock infected cells.

Preparation of Cells.

MT2 cells are infected with the LAI strain of HIV at a multiplicity of infection of 0.01 in complete RPMI containing 2 mg/mL polybrene for 2 hours at 37° C. Following infection, cells diluted to $2.5 \times 10^5$ cells/mL in complete RPMI media. 100 mL of the cell suspension are seeded onto 96 well plates, $2.5 \times 10^4$ cells/well, containing test compounds as described above. The final volume in each well is 200 mL. Plates are sealed and incubated at 37° C. in a humidified 5% $CO_2$ incubator for 5 days.

Developing the Assay.

Following the 5 day incubation, 80 mL of cell free supernatant is removed from each well and 10 mL of a 5 mg/mL solution of MTT is added. The plates are returned to the incubator for 2 hours followed by the addition of 100 mL of acidified isopropanol (10% Triton X-100 plus 0.1N HCl in anhydrous isopropanol) to each well. Formazan crystals are dissolved by repeated pipetting in the wells. Plates are read at 570 nm in a Biotek plate reader.

Calculation of Data.

Figure 2:
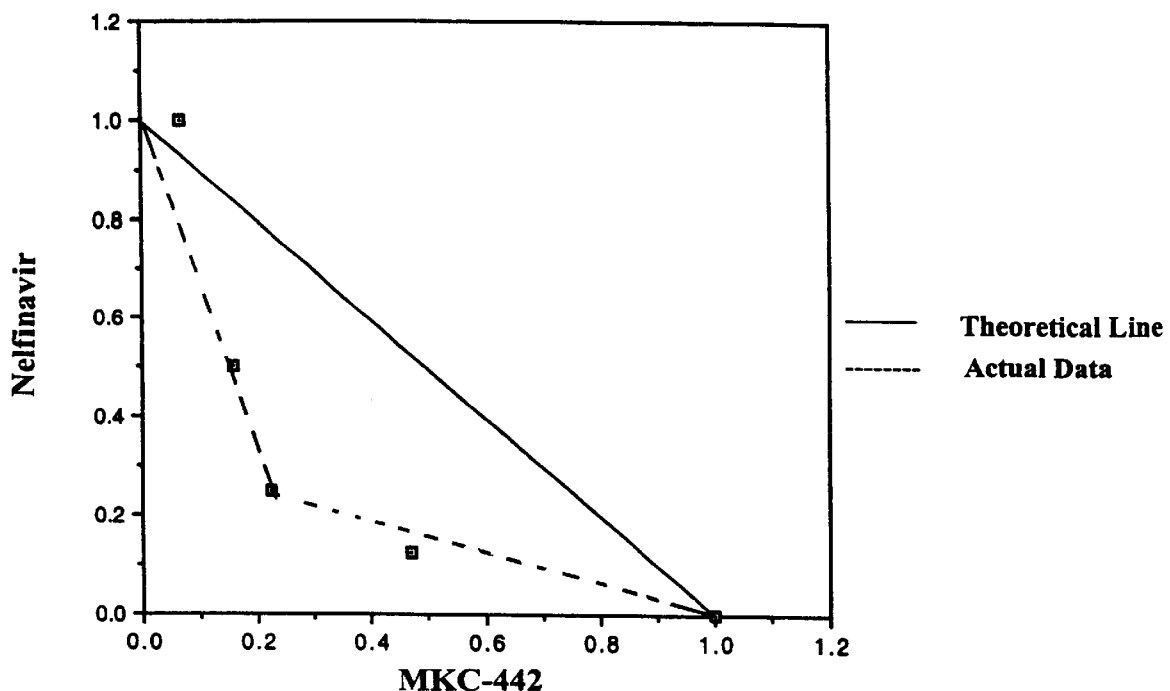
FIG. 2 is an isobologram analysis of the combination of MKC-442 and nelfinavir in cell culture.

A dose response curve for each individual compound is generated using the absorption values of the cell controls as 100% protection and no drug virus infected cells as 0% protection. From this dose response curve a $EC_{50}$ value is calculated and is defined as the concentration of drug that inhibits 50% of viral induced CPE. The effects of the combined compounds were obtained using the isobologram technique (Elion, G.B. et al, 1954, J. Biol. Chem., 208: 477–488). The data plotted were obtained by dividing the $EC_{50}$ of compound #1 in the presence of a fixed concentration of compound #2 by the $EC_{50}$ of compound #1 alone. In a similar fashion data can be obtained by dividing the $EC_{50}$ of compound #2 in the presence of a fixed concentration of compound #1 by the $EC_{50}$ of compound #2 alone. The $EC_{50}$ ratios are plotted against the ratio of compound at each combination. If the curve generated by these points falls on the theoretic diagonal line, the combination is additive. If the curve is above the theoretical line, the combination is antagonistic. And, if the curve lies below the theoretical line, then the combination is synergistic. FIGS. 1 and 2 illustrate isobologram analysis of the combination of MKC-442 with indinavir and with nelfinavir.

Even though a combination exhibits additive and not synergistic effects according to this assay, the combination can still provide an effect that is different from the separate administration of the two agents. For example, the biodistribution, pharmacokinetics, or metabolism of one can be affected by the other. Further, MKC-442 is advantageously delivered in combination or alternation with another antiviral agent that exhibits a different mutation profile than MKC-442.

PREPARATION OF PHARMACEUTICAL COMPOSITIONS

Humans suffering from effects caused by any of the diseases described herein, and in particular, HIV infection, can be treated by administering to the patient an effective amount of MKC-442 in combination with one or more agents described above or a phannaceutically acceptable derivative or salt thereof in the presence of a pharmaceutically acceptable carrier or diluent. The active materials can be administered by any appropriate route, for example, orally, parenterally, enterally, intravenously, intradermally, subcutaneously, or topically, in liquid or solid form.

The active compounds are included in the pharmaceutically acceptable carrier or diluent in an amount sufficient to deliver to a patient a therapeutically effective amount of compound to inhibit viral replication in vivo, especially HIV replication, without causing serious toxic effects in the treated patient. By "inhibitory amount" is meant an amount of active ingredient sufficient to exert an inhibitory effect as measured by, for example, an assay such as the ones described herein.

A preferred dose of the compounds for all the above-mentioned conditions will be in the range from about 1 to 50 mg/kg, preferably 1 to 20 mg/kg, of body weight per day, more generally 0.1 to about 100 mg per kilogram body weight of the recipient per day. The effective dosage range of the pharmaceutically acceptable derivatives can be calculated based on the weight of the parent nucleoside to be delivered. If the derivative exhibits activity in itself, the effective dosage can be estimated as above using the weight of the derivative, or by other means known to those skilled in the art.

The compounds are conveniently administered in unit any suitable dosage form, including but not limited to one containing 7 to 3000 mg, preferably 70 to 1400 mg of active ingredient per unit dosage form. An oral dosage of 50 to 1000 mg is usually convenient.

Ideally, the active ingredients should be administered to achieve peak plasma concentrations of the active compound of from about 0.2 to 70 $\mu$M, preferably about 1.0 to 10 $\mu$M. This may be achieved, for example, by the intravenous injection of a 0.1 to % solution of the active ingredient, optionally in saline, or administered as a bolus of the active ingredient.

The concentration of active compound in the drug composition will depend on absorption, distribution, metabolism and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein arc exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible bind agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compounds can be administered as a component of an elixir, suspension, syrup, wafer, chewing gum or the like. A syrup may contain, in addition to the active compounds, sucrose as a sweetening agent and certain preservatives, dyes and colorings and flavors.

The compounds or their pharmaceutically acceptable derivative or salts thereof can also be mixed with other active materials that do not impair the desired action, or with materials that supplement the desired action, such as antibiotics, antifungals, antiinflammatories, protease inhibitors, or other nucleoside or non-nucleoside antiviral agents, as discussed in more detail above. Solutions or suspensions used for parental, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanydrides, polyglycolic acid, collagen, polyorthoesters, and polylactic acid. Methods for preparation of such formulations will be apparent to those skilled in the art. The materials can also be obtained commercially from Alza Corporation.

Liposomal suspensions (including liposomes targeted to infected cells with monclonal antibodies to viral antigens) are also preferred as pharmaceutically acceptable carriers. these may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

This invention has been described with reference to its preferred embodiments. Variations and modifications of the invention, will be obvious to those skilled in the art from the foregoing detailed description of the invention. It is intended that all of these variations and modifications be included within the scope of this invention.

We claim:

1. A method for the treatment of a patient infected with HIV, comprising administering an effective treatment amount of MKC-442 or its pharmaceutically acceptable salt in combination or alternation with a compound selected from the group consisting of abacavir, FTC or d4T or its pharmaceutically acceptable salt.

2. The method of claim 1, wherein the compound is FTC.

3. A pharmaceutical composition for the treatment of a patient infected with HIV, comprising an effective treatment amount of MKC-442 or its pharmaceutically acceptable salt in combination or alternation with a compound selected from the group consisting of abacavir, FTC or d4T or its pharmaceutically acceptable salt.

4. The composition of claim 3, wherein the compound is FTC.

5. The method of claim 1, wherein the compound is abacavir.

6. The composition of claim 3, wherein the compound is abacavir.

7. The method of claim 1, wherein the compound is d4T.

8. The composition of claim 3, wherein the compound is d4T.

* * * * *